United States Patent [19]

Escobar et al.

[11] Patent Number: 5,017,609

[45] Date of Patent: May 21, 1991

[54] PHARMACEUTICAL COMPOSITION AND METHOD OF TREATMENT OR PROPHYLAXIS OF CARDIAC DISORDERS

[75] Inventors: Agustin Escobar, Aquadilla, P.R.; Dietmar Wagenknecht, Zion, Ill.; Ahmad W. Malick, Edison, N.J.

[73] Assignee: E. I. Du Pont de Nemours and Company, Wilmington, Del.

[21] Appl. No.: 437,293

[22] Filed: Nov. 16, 1989

Related U.S. Application Data

[63] Continuation of Ser. No. 289,501, Dec. 23, 1988, abandoned, which is a continuation of Ser. No. 810,547, Dec. 18, 1985, abandoned, which is a continuation-in-part of Ser. No. 598,061, Apr. 9, 1984, abandoned.

[51] Int. Cl.$^5$ .............................................. A61K 31/24
[52] U.S. Cl. ..................................... 514/538; 514/821
[58] Field of Search ............... 514/510, 511, 522, 524, 514/529, 532, 534, 538, 821

[56] References Cited

U.S. PATENT DOCUMENTS

| | | | |
|---|---|---|---|
| 3,742,023 | 6/1973 | Koppe et al. | 260/471 R |
| 3,872,147 | 3/1975 | Koppe et al. | 260/465 |
| 4,146,630 | 3/1979 | Kampe et al. | 546/207 |
| 4,191,765 | 3/1980 | Fritsch et al. | 424/248.53 |
| 4,346,093 | 8/1982 | Friebe et al. | 546/271 |
| 4,387,103 | 6/1983 | Erhardt et al. | 560/22 |
| 4,829,086 | 5/1989 | Bodor | 514/538 |

FOREIGN PATENT DOCUMENTS 0041491 12/1981 European Pat. Off. ............ 514/538

OTHER PUBLICATIONS

Remington's Pharmaceutical Sciences, 16th ed. (1980), pp. 214, 238, 1253–1256 and 1463–1468.
Morrison and Boyd, *Organic Chemistry*, 3rd Edition, Sec. 20.16, p. 675.
L. H. Smith, *Journal of Applied Chemistry and Biotechnology*, 28(3):201–212 (1978).
Hisashi Nogami et al., *Chemical and Pharmaceutical Bulletin*, vol. 10, pp. 1158–1160 (1962).
Joseph M. Talmage et al., *Journal of Pharmaceutical Sciences*, vol. 57, No. 6, pp. 1073–1074 (Jun. 1968).
*Pharmaceuticals*, vol. 66, p. 6499, 68878k (1967).
H. A. Garrera et al., *Rev. Latinoamer, Quim.*, 7:4–8 (1976).
P. B. Sheth et al., *Journal of Pharmaceutical Sciences*, vol. 56, No. 8, pp. 983–986 (Aug. 1967).
M. Balakrishnan et al., *Tetrahedron Letters*, No. 45, pp. 4617–4620 (1972).
H. A. Garrera et al., *Rev. Latinoamer, Quim.*, 5:201–205 (1974).

*Primary Examiner*—Joseph A. Lipovsky
*Attorney, Agent, or Firm*—Bernard, Rothwell & Brown

[57] ABSTRACT

A pharmaceutical composition is disclosed, which contains a short-acting β-blocking compound of the formula

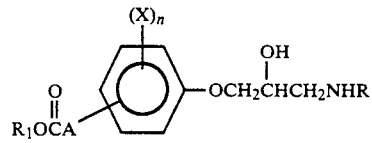

wherein $R_1$ may be an alkyl, cycloalkyl, alkenyl, alkynyl, alkyl carboxymethyl, aryl carboxymethyl, aryl or aralkyl, A may be an alkylene or alkenylene, X may be independently amino, hydrogen, halogen, hydroxy, alkoxy, aryloxy, aralkyl, cyano, amido or trifluoromethyl, n is an integer from 1 to about 4, R may be an alkyl, propargyl, dimethylpropargyl or hydroxyalkyl; or a pharmaceutically acceptable salt thereof in a hydroalcoholic solution further containing a physiologically acceptable buffering agent, ethanol and a physiologically acceptable liquid polyhydric compound. A method for treatment or prophylaxis of cardiac disorders using the composition of the present invention is also disclosed.

10 Claims, 2 Drawing Sheets

PHARMACEUTICAL COMPOSITION AND METHOD OF TREATMENT OR PROPHYLAXIS OF CARDIAC DISORDERS

This is a continuation of application Ser. No. 07/289,501, filed Dec. 23, 1988, now abandoned which is a continuation of application Ser. No. 810,547, filed Dec. 18, 1985, now abandoned which is a continuation-in-part of Ser. No. 598,061, filed Apr. 9, 1984, now abandoned.

BACKGROUND OF THE INVENTION

The present invention relates to pharmaceutical compositions which contain short-acting β-adrenergic blocking agents. More particularly, the invention concerns novel compositions in which ester-containing β-blocking drugs are stabilized against hydrolysis during shipping and storage.

In the past, the emphasis in β-blocker research has been to develop stable drugs which could be administered to cardiac patients over relatively long periods of time. However, often it is desirable in the critical care setting to quickly reduce heart work or improve rhythmicity during a cardiac crisis, e.g., during or shortly after a myocardial infarction. Conventional β-blocking agents can be employed for such treatment, but their long durations of action can cause undesirable side effects.

Recently, certain compounds containing ester functions have been found to possess β-adrenergic blocking activity. (See U.S. Pat. No. 4,387,103 to Erhardt, et al., June 7, 1983.) These compounds generally have a short duration of action in vivo, and do not possess the disadvantages of the conventional β-blockers described above. The ester groups in these compounds have, however, been found to be somewhat unstable in aqueous environments, such as intravenous infusion solutions. The practical effect of this instability is that conventional compositions containing the compounds have relatively short shelf lives, thus making commercial distribution and storage difficult.

Therefore, there remains a need for pharmaceutical preparations of short-acting β-blockers which are stable in vitro and have a relatively long storage life.

SUMMARY OF THE INVENTION

In accordance with the present invention, disclosed herein is a pharmaceutical composition for the treatment or prophylaxis of cardiac disorders in a mammal comprising from about 0.1 to about 30% by weight of a β-adrenergic blocking compound having the formula

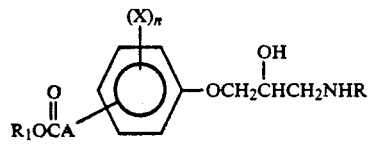

where $R_1$ is an alkyl having from 1 to about 6 carbon atoms, cycloalkyl of from 3 to about 5 carbon atoms, alkenyl of from 2 to about 5 carbon atoms, alkynyl of from 3 to about 5 carbon atoms, alkyl carboxymethyl where the alkyl is from 1 to about 5 carbon atoms, aryl carboxymethyl in which the aryl portion contains from 6 to about 10 carbon atoms, aryl of from 6 to about 10 carbon atoms, or aralkyl wherein the alkyl portion contains from 1 to about 6 carbon atoms and the aryl portion represents substituted or unsubstituted monocyclic or polycyclic aromatic ring systems of from 6 to about 10 carbon atoms; A is an alkylene from about 1 to about 5 carbon atoms, or alkenylene of from 2 to about 5 carbon atoms; X is independently amino, hydrogen, halogen, hydroxy, alkoxy, aryloxy, aralkyl, cyano, amido, or trifluoromethyl; n is an integer from 1 to about 4; R is alkyl having from 1 to about 5 carbon atoms, propargyl, dimethylpropargyl, or hydroxyalkyl having from 1 to about 6 carbon atoms; and its pharmaceutically acceptable salts in a hydroalcoholic solution further comprising from about 0.05 to about 2 molar physiologically acceptable buffering agent; from about 5 to about 60% by volume ethanol; from about 5 to about 60% by volume of a physiologically acceptable liquid polyhydric compound; and said hydroalcoholic solution having a pH of from about 4.0 to about 6.0. A method for the treatment or prophylaxis of cardiac disorders in a mammal comprising parenteral administration of the composition of the invention to such mammal is also disclosed.

DETAILED DESCRIPTION OF THE INVENTION

Figure 1:
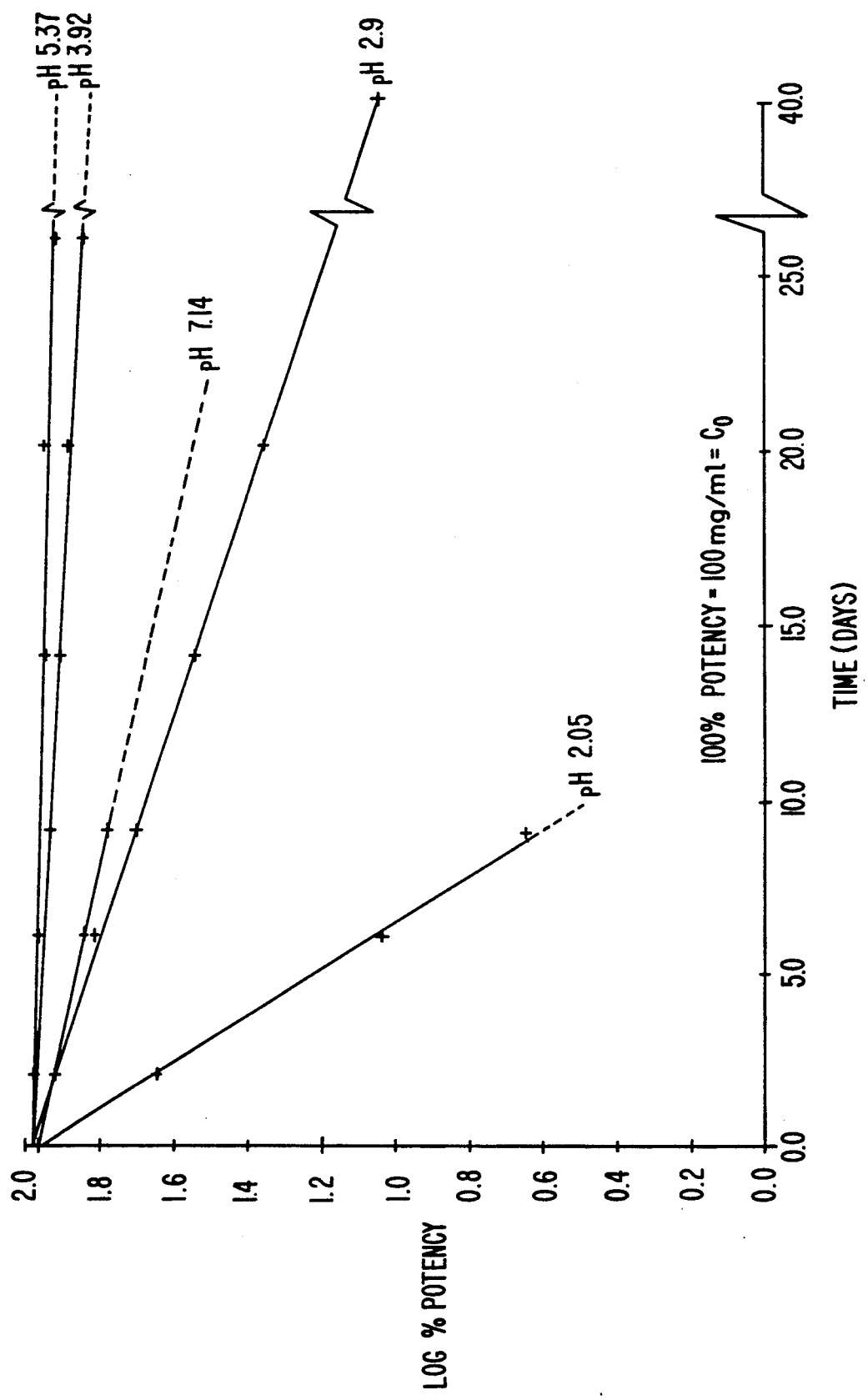
FIG. 1: A graphic depiction of the effect of various pH levels on the potency of methyl 3-(p-phenoxypropanolamine) propionate over time.

In accordance with the present invention, it has been discovered that a stable pharmaceutical composition possessing a relatively long shelf life can be prepared using short-acting, ester-containing β-blockers of the formula:

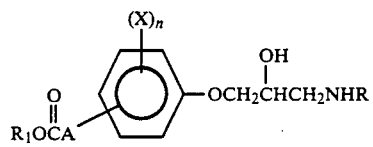

where $R_1$ may be an alkyl having from 1 to about 6 carbon atoms such as methyl, ethyl, propyl, t-butyl, isopentyl, and the like; cycloalkyl of from 3 to about 5 carbon atoms such as cyclopropyl, cyclopentyl, methyl cyclopropyl, and the like; alkenyl of from 2 to about 5 carbon atoms such as ethenyl, propenyl, 2-methyl-2-butenyl, and the like; alkynyl of from 3 to about 5 carbon atoms such as ethynyl, propynyl, 3-methyl-1-butynyl, and the like; alkyl carboxymethyl where the alkyl is from 1 to about 5 carbon atoms such as methyl carboxymethyl, ethyl carboxymethyl, propyl carboxymethyl, and the like; aryl carboxymethyl in which the aryl portion contains from 6 to about 10 carbon atoms such as phenyl carboxymethyl, napthyl carboxymethyl and the like; aryl of from 6 to about 10 carbon atoms such as phenyl, 2-tolyl, 2-methoxyphenyl, naphthyl, and the like; or aralkyl in which the alkyl portion contains from 1 to about 6 carbon atoms and the aryl portion represents substituted or unsubstituted monocyclic or polycyclic aromatic ring systems of from 6 to about 10 carbon atoms such as benzyl, phenethyl, 1-naphthylpropyl, 3,4-dimethoxyphenethyl, naphthylethyl, and the like.

A may be an alkylene from about 1 to about 5 carbon atoms such as methylene, ethylene, propylene, and the like; or alkenylene of from 2 to about 5 carbon atoms such as ethenylene, propenylene, isobutylenylene, and the like.

X is independently amino, hydrogen, halogen, hydroxy, alkoxy of from about 1 to about 10 carbon atoms such as methoxy, ethoxy and the like, of from about 6 to about 10 carbon atoms such as phenyloxy and the like, wherein the alkyl portion contains from 1 to about 6 carbon atoms and the aryl portion contains from 6 to about 10 carbon atoms such as phenylmethyl, p-methylbenzylmethyl dimethylbenzyl, phenyl t-butyl, 3,4-dimethoxyphenethyl and the like, (preferably dimethylbenzyl, phenyl t-butyl, 3,4-dimethoxyphenethyl), cyano, amido, or trifluoromethyl, and n is an integer from 1 to about 4.

R may be an alkyl having from 1 to about 5 carbon atoms such as methyl, ethyl, propyl, t-butyl, isopentyl, and the like; propargyl; dimethylpropargyl; or hydroxyalkyl having from 1 to about 6 carbon atoms such as hydroxymethyl, hydroxyethyl, 2-hydroxypentyl and the like.

In preferred compounds, $R_1$ is ethyl or methyl, A is ethylene, X is hydrogen, the

group is in the para position with respect to the side chain containing the —R group, and/or —R is represented by —W—B where —W— is an alkylene containing from 1 to about 10 carbon atoms, and —B is —NR$_2$COR$_3$, —NR$_2$CONR$_3$R$_4$, —NR$_2$SO$_2$R$_3$, —NR$_2$SO$_2$NR$_3$R$_4$, —NR$_2$COOR$_5$ or —NHR$_6$, where R$_2$, R$_3$, R$_4$ and R$_5$ may each be hydrogen, lower alkyl of from about 1 to about 10 carbon atoms, lower alkoxyalkyl of from 1 to about 10 carbon atoms, lower alkoxyaryl wherein the alkoxy portion contains from 1 to about 6 carbon atoms and the aryl portion contains from 6 to about 10 carbon atoms, lower cycloalkyl of from 3 to about 10 carbon atoms, lower alkenyl of from 1 to about 10 carbon atoms, lower alkynyl of from 1 to about 10 carbon atoms, aryl of from 6 to about 10 carbon atoms, heteroaryl of from about 4 to about 10 carbon atoms or aralkyl wherein the alkyl portion contains from 1 to about 6 carbon atoms and the aryl portion contains from 6 to about 10 carbon atoms, except that R$_3$ and R$_5$ are not hydrogen when B is —NR$_2$SO$_2$R$_3$ or —NR$_2$COOR$_5$, or R$_3$ and R$_4$ may together with N form a 5-to 7-membered heterocyclic group, and R$_6$ is unsubstituted or substituted pyridinyl, phenyl, naphthyl or indoyl the optional R$_6$ substituents being the same as X defined above. In one embodiment, R$_2$, R$_3$, R$_4$ and R$_5$ are hydrogen, or R$_3$ and R$_4$ together with N form a 5-7 membered heterocyclic group.

In one embodiment, R$_1$ is lower alkyl of from 1 to about 5 carbon atoms or lower alkenyl of from 2 to about 5 carbon atoms; A is alkylene of up to about 3 carbon atoms; X is lower alkyl of from 1 to about 10 carbon atoms, lower alkenyl of from 2 to about 10 carbon atoms, lower alkynyl of from 2 to about 10 carbon atoms, lower alkoxy of from 1 to about 10 carbon atoms, halogen, acetamido, amino, nitro, alkylamino of from 1 to about 10 carbon atoms, hydroxy, lower hydroxyalkyl of from 1 to about 10 carbon atoms, or cyano; n is an integer of from about 1 to about 4; R is lower alkyl of from 1 to about 10 carbon atoms or aralkyl wherein the alkyl portion contains from about 1 to about 6 carbon atoms and the aryl portion contains from about 6 to about 10 carbon atoms. According to this embodiment, the R$_1$-containing group preferably is in the ortho- or para-position with respect to the R-containing group. Preferably, R$_1$ is a lower alkyl or alkenyl group having from 1 to about 3 carbon atoms, and X is hydrogen, lower alkoxy of from 1 to about 5 carbon atoms, lower alkyl of from 1 to about 5 carbon atoms, halogen or cyano. When the X substituent is a halogen, X preferably is fluorine. R$_1$ preferably is methyl or ethyl, with methyl being particularly preferred. According to this embodiment, R preferably is lower alkyl of from 1 to about 5 carbon atoms or aralkyl wherein the alkyl portion contains from 1 to about 5 carbon atoms and the aryl portion contains from 6 to about 10 carbon atoms. In particularly preferred embodiments, R is isopropyl, t-butyl or 3,4-dimethoxyphenethyl, and X is hydrogen with n being 4. When R$_1$ is methyl or ethyl, A preferably is ethylene, and R is isopropyl, t-butyl or 3,4-dimethoxyphenethyl. Most preferably, R is isopropyl.

Methods for producing the above-described compounds are known in the prior art. For example, U.S. Pat. No. 4,387,103 to Erhardt et al. (incorporated herein by reference) discloses methods for preparing above-defined compounds wherein A is alkylene. Methods for preparing above-defined compounds wherein A is alkenylene are described in U.S. Pat. No. 4,191,765 to Fritsch et al. (incorporated herein by reference).

The above-described β-blocking compounds may be separated into optically active enantiomers using conventional methods. While both configurations are active β-blockers, the l-isomers have been found to be more active than their dextrorotary counterparts.

In one embodiment of the present invention, the composition contains a pharmaceutically acceptable acid addition salt of an above described β-blocking compound, e.g., a hydrochloride, sulfate, phosphate, gluconate, tartrate, etc. salt.

The composition of the present invention consists of a hydroalcoholic solution containing an above described β-blocking compound (or its pharmaceutically acceptable salt) at a concentration of from about 0.1 to about 30% by weight. Concentrations of less than about 0.1% (weight) of the β-blocking compounds in solutions generally do not provide effective β-blocking activity at practical infusion rates, while there is generally no added benefit to having concentrations greater than about 30% (weight) of the β-blocker in solution. In particularly preferred compositions, the concentration of β-blocking compound in solution is from about 1 to about 30% by weight.

One component of the hydroalcoholic solution is ethanol, preferably at a concentration of from about 5 to about 60% by volume. Ethanol has been found to be important in the stabilization of the β-blocking compound according to the present invention.

The hydroalcoholic solution also contains a physiologically acceptable liquid polyhydric compound, preferably at a concentration of from about 5 to about 60% by volume. Physiologically acceptable liquid polyhydric compounds include, but are not limited to, alkyls of from 1 to about 10 carbon atoms having two or more adjacent hydroxyl groups such as ethylene glycol, propylene glycol, glycerol and the like; polyethyleneglycols having a molecular weight of from about 200 to about 600 daltons; and glycerin. Preferred liquid polyhydric compounds include alkyls of from 1 to about 10 carbon atoms having two or more adjacent hydroxyl groups, and polyethyleneglycols having a molecular weight of from about 200 to about 600 daltons. Glycerin is less preferred, because solutions containing it have been observed to discolor on storage at 55° C. A particularly preferred liquid polyhydric compound is propylene glycol. Liquid polyhydric compounds, in conjunction with ethanol are useful stabilizing components of the β-blocking compounds in the hydroalcoholic solution according to the present invention. In particularly preferred compositions, the volume ratio of ethanol to the liquid polyhydric compound is about 1:1.

Stability of the β-blocking compound in solution is affected by the pH of the solution. In preferred compositions, the pH of the hydroalcoholic solution ranges from about 4.0 to about 6.0. When the pH of the solution is less than about 4.0 or greater than about 6.0, degradation of the β-blocking compound was observed. In particularly preferred compositions, the pH ranges from about 4.6 to about 5.4, and in most preferred compositions, the pH ranges from about 4.9 to about 5.1. The pH is preferably maintained by a physiologically acceptable buffering agent at a concentration of from about 0.05 to about 2 molar. Preferred buffering agents include acetate buffers, such as sodium acetate and acetic acid; trishydroxymethylaminomethane; sodium phosphate (mono and dibasic); phosphoric acid; sodium citrate; citric acid; and amphoteric compounds such as glycine, cystine and the like. Acetate buffers are particularly preferred. The molar ratio of the β-blocking compound to buffering agent advantageously is about 3:1.

The β-blocking compounds used in the pharmaceutical compositions of the present invention are surprisingly rendered quite stable by the hydroalcoholic solution of the present invention. Typical compositions exhibit shelf lives from 20 to 36 months, compared to 2 to 3 months for the same compounds in conventional preparations. These compositions thus facilitate commercial distribution and storage of the above described short-acting ester-containing β-blockers.

The pharmaceutical compositions of the present invention are preferably added to a physiologically acceptable infusion medium to a final concentration of β-adrenergic compound of from about 50 μg/ml/min to about 600 μg/ml/min percent by weight, and thereby parenterally administered to the patient.

The dosages and rates of administration of these compositions generally depend upon the patient's needs and the particular β-blocking compound employed. These dosages and rates of administration are described in the above-mentioned U.S. Pat. No. 4,387,103.

The invention is further illustrated by the following examples, which are not intended to be limiting.

EXAMPLE I

The Effect of pH on the Degradation of Methyl 3-(p-Phenoxypropanolamine) proprionate The kinetics of degradation of methyl-3-(p-Phenoxypropanolamine) propionate (sometimes referred to as "the drug") in five aqueous buffers at 55° C. was studied. All buffer solutions were prepared in Water for Injection, USP (deionized and distilled water). Five buffer solutions, pH 2.16, 3.05, 4.08, 5.63 and 7.44 were prepared by combining various amounts of 0.1M citric acid and 0.2M disodium hydrogen phosphate solutions (Table I).

In each case an appropriate amount of methyl-3-(p-Phenoxypropanolamine) propionate to give a final concentration of 100 mg/ml was accurately weighed and transferred to a calibrated flask. The buffer solution was then added to the flask and the contents stirred until the drug had completely dissolved. The pH of each solution was determined, this data is given in Table I. Each buffered drug solution was filled into 5 ml flint ampuls. The ampuls were partially filled with 3 ml of solution and then sealed. Sufficient ampuls were prepared so that there was at least one for each stability time. Samples of all five solutions were placed in a 55° C. oven. At each stability time one ampul of each solultion was removed. The pH, potency and the physical appearance of the solutions was determined. The concentration of the drug was determined by a high performance liquid chromatographic (HPLC) method. The physical appearance of the solutions remained unchanged at all stability times.

The kinetic data obtained was plotted as a log of drug concentration versus time. The apparent first-order rate constants were calculated from the slopes of the linear regression lines fitted to $\log (C) = \log (Co) - 2.303 \, kt$ where C is drug concentration at time t, Co is the initial drug concentration and k is the apparent first-order rate constant. This method was also used for Examples II through V.

The kinetics of degradation of the drug at 55° C. and at various pH values was followed by monitoring the potency of the drug at different stability times. The logarithm of the potency versus time in all cases produced linear plots. These data are shown in FIG. 1. The apparent first-order rate constants were calculated from the slopes of the linear regression lines and are presented in Table II. The maximum change in the pH, which in all cases occurred when the sample for the last data point was obtained, is also given in Table II.

Figure 2:
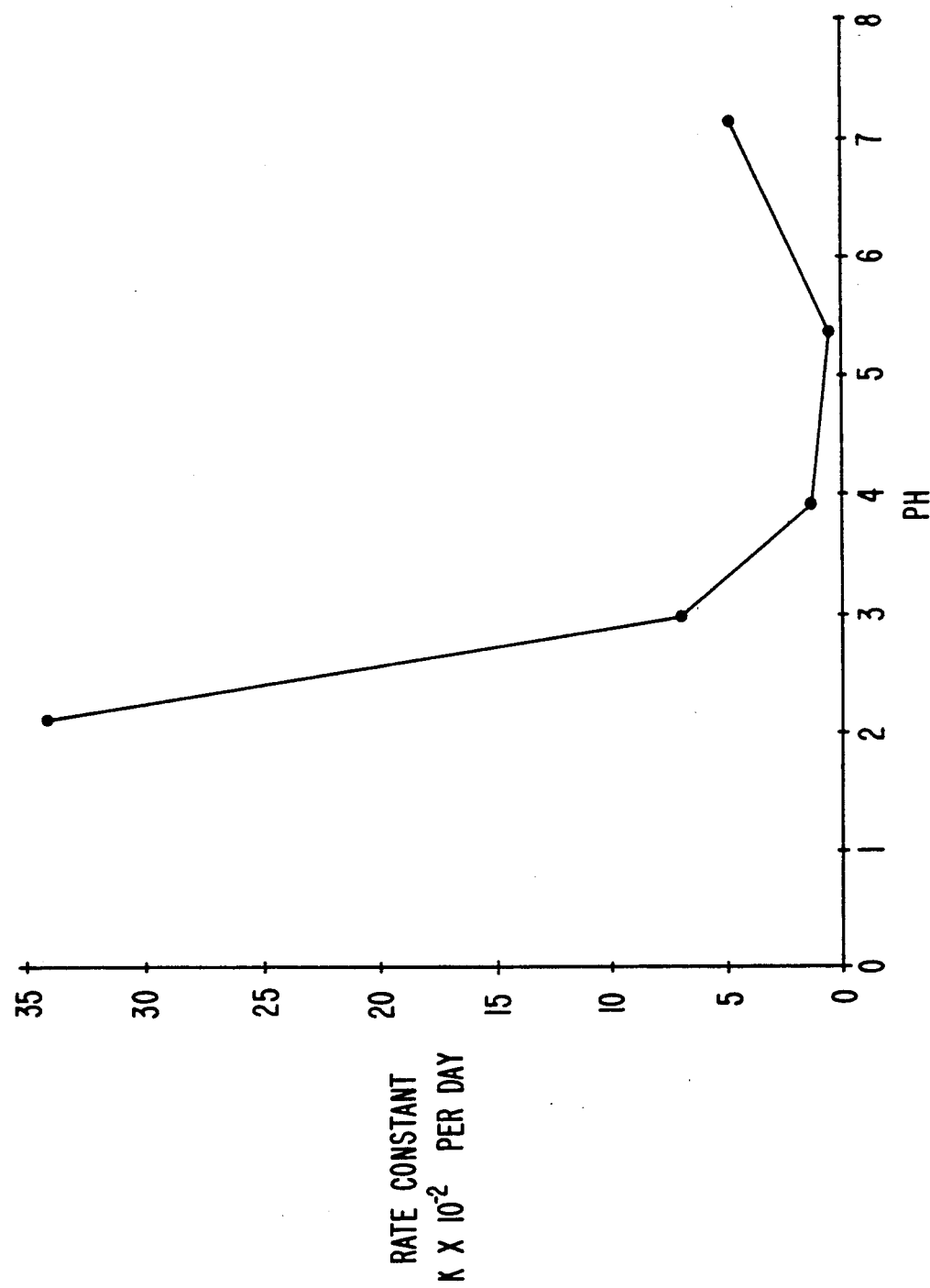
FIG. 2: A graphic depiction of rate of degradation of methyl 3-(p-phenoxypropanolamine) propionate at 55° C. and at various pH levels.

The pH rate profile at 55° C. for the drug is presented in FIG. 2. The line joining the data points is only drawn to show the trend and does not represent actual data. The degradation rate increases both at low and high pH values in the range studied (pH 2.0514 7.14). This may be due to acid or base catalysed hydrolysis at the two extremes. The lowest rate observed in this study at pH 5.37 is almost 64 times slower than the highest observed at pH 2.05.

TABLE I pH of Citrate-Phosphate Buffers Used

| | Composition No. | | | | |
|---|---|---|---|---|---|
| | 1 | 2 | 3 | 4 | 5 |
| Amount of Dibasic Sodium Phosphate, Heptahydrate ($Na_2HPO_4.7H_2O$) (wt %) | 0.06 | 1.00 | 2.4 | 3.09 | 4.83 |
| Amount of Citric Acid, Monohydrate ($H_3C_6H_5O_7.H_2O$) (wt %) | 2.08 | 1.69 | 1.30 | 0.89 | 0.21 |
| pH of Buffer Solution | 2.16 | 3.05 | 4.08 | 5.63 | 7.44 |
| Amount of the Drug (wt %) | 10 | 10 | 10 | 10 | 10 |
| pH of buffer Solution Containing Dissolved Drug | 2.05 | 2.97 | 3.92 | 5.37 | 7.14 |

TABLE II

Apparent First Order Rate Constants For Hydrolysis of the Drug in Buffers at 55° C.

| pH | 1 | 2 | 3 | 4 | 5 |
|---|---|---|---|---|---|
| pH | 2.05 | 2.97 | 3.92 | 5.37 | 7.14 |
| k, day$^{-1}$ × 10$^{-2}$ | 34.01 | 7.03 | 1.30 | 0.53 | 4.8 |
| t½, day | 2.04 | 9.87 | 53.16 | 130.40 | 14.44 |
| r$^a$ | 0.9991 | 0.9995 | 0.9916 | 0.9375 | 0.9988 |
| Δph$^b$ | −0.04 | −0.22 | −.028 | 0.71 | −0.89 |

$^a$Correlation coefficient for the linear regression
$^b$Difference between initial and final pH (terminal sample).

EXAMPLE II

Stability of Methyl 3-(p-Phenoxypropanolamine) propionate (the drug) in One or Two Component Vehicles Containing Ethanol and Citrate-Phosphate Buffer (pH 4.0)

Stability of the drug in 10% (V/V) alcohol in buffer, 30% (V/V) alcohol in buffer and ethanol, USP is given in Table III. It can be seen from the data in Table III, that incorporation of 10% ethanol in the buffer increases the stability of the drug. The stabilizing effect is quite dramatic when ethanol content is increased to 30% V/V, in this case the degradation rate is almost one third of the rate in buffered solution without ethanol. When the drug was formulated in just ethanol, USP, the stability was marginally worse than 30% ethanol in buffer vehicle. This suggests that the stabilization effect is maximized at certain ethanol concentrations in the vehicle and beyond that no benefit is to be gained by adding more ethanol in the formulation. In addition, in the all ethanol formulation the HPLC tracing revealed evidence of transesterification of the drug to an ethyl ester.

TABLE III

Apparent First-Order Rate Constants (55° C.) for The Degradation of the drug (100 mg/ml) In Vehicles Containing Phosphate-Citrate Buffer (pH 4.0) and/or Ethanol, USP

| Formulation | k × 10$^2$, day$^{-1}$* | t½, day* | r$^a$* | Time Span of Study (Days) |
|---|---|---|---|---|
| Phosphate-Citrate buffer (pH 4.0) | 1.304 | 53.2 | 0.9375 | 26 |
| Buffer Containing 10% V/V Ethanol, USP | 1.071 | 64.7 | 0.9896 | 38 |
| Buffer Containing 30% V/V Ethanol, USP | 0.411 | 168.7 | 0.9474 | 24 |
| Ethanol, USP | 0.516 | 134.4 | 0.9703 | 44 |

$^a$Correlation coefficient of the linear regression line.
*See Example I

EXAMPLE III

Stability of Methyl 3-(p-Phenoxypropanolamine) propionate (the drug) in Vehicles Containing Citrate Phosphate Buffer (0.16M, pH 5.4) and Propylene Glycol (PG)

Stability of the drug was investigated in vehicles containing varying amounts of citrate-phosphate buffer and propylene glycol (PG) (Table IV). The proportion of PG in these mixtures varied from 10% to 70%. Increasing the PG concentration increases the stability of the drug. Within the range studied there is a linear relationship between stability of the drug and PG content in the vehicle.

Table IV also presents stability of the drug in a vehicle containing 50% (V/V) PG in water. When this is compared to the drug stability in a vehicle containing 50% V/V PG in citrate-phosphate buffer, it can be seen that the half-life in the buffered formulation is almost twice as long.

The data presented in this section shows that PG has a significant stabilizing effect on the drug.

TABLE IV

Apparent First-Order Rate Constants (55° C.) for The Degradation of the drug (100 mg/ml) in Vehicles Containing Citrate-Phosphate Buffer (0.16M, pH 5.4) and Propylene Glycol (PG)

| Formulation | k × 10$^2$, day$^{-1}$* | t½, day* | r$^a$* | Time Span of Study (Days) |
|---|---|---|---|---|
| PG 70%, Buffer 30% V/V | 0.423 | 161.2 | 0.9968 | 135 |
| PG 50%, Buffer 50% V/V | 0.616 | 112.6 | 0.9989 | 135 |
| PG 30%, Buffer 70% V/V | 0.769 | 90.2 | 0.9997 | 135 |
| PG 10%, Buffer 90% V/V | 0.949 | 73.1 | 0.9992 | 52 |
| PG 50%, Water 50% V/V | 1.371 | 50.6 | 0.9903 | 18 |

$^a$Correlation coefficient of the linear regression line.
*See Example I

EXAMPLE IV

Stability of Methyl 3-(p-Phenoxypropanolamine) propionate (the drug) in Vehicles Containing Citrate-Phosphate Buffer (0.16M, pH 5.4) and either PEG200 or Propylene Glycol (PG)

Table V presents stability data of the drug in 50% (V/V) PEG 200 in buffer, and 50% (V/V) Propylene Glycol in buffer. The greatest stability observed was in the case of the formulation containing propylene glycol (PG).

TABLE V

Apparent First-Order Rate Constants (55° C.) for The Degradation of the drug (100 mg/ml) in Vehicles Containing Citrate-Phosphate Buffer (0.16M, pH 5.4) and either PEG 200 or Propylene Glycol

| Formulation | k × 10$^2$, day$^{-1}$* | t½, day* | r$^a$* | Time Span of Study (Days) |
|---|---|---|---|---|
| PEG 200 50%, Buffer 50% V/V | 0.793 | 87.4 | 0.9796 | 44 |
| Propylene Glycol 50%, Buffer 50% V/V | 0.616 | 112.6 | 0.9989 | 135 |

$^a$Correlation coefficient of the linear regression line.
*See Example I

EXAMPLE V

Stability of Methyl 3-(p-Phenoxypropanolamine) propionate (the drug) in One, Two or Three Component Vehicles Containing Ethanol, Propylene Glycol (PG) and Citrate-Phosphate Buffer (0.16M, pH 5.4) or Water The stability of the drug was studied first in two systems, the first vehicle consisted of 70% (V/V) PG and 30% (V/V) ethanol whereas the second was 50:50 mixture of the two. The results are given in Table VI. It can be seen that the stability of the drug in the 50:50 mixture was greater.

TABLE VI

Apparent First-Order Rate Constants (55° C.) for
The Degradation of the drug (100 mg/ml) in One, Two or
Three Component Vehicles Containing Ethanol,
Propylene Glycol (PG) and Citrate-Phosphate Buffer
(0.16M, pH 5.4) or Water

| Formulation | $k \times 10^2$, day$^{-1*}$ | $t_{\frac{1}{2}}$, day* | $r^{a*}$ | Time Span of Study (Days) |
|---|---|---|---|---|
| PG 70%, Ethanol$^b$ 30% V/V | 0.118 | 586.7 | 0.8615 | 119 |
| PG 50%, Ethanol$^b$ 50% V/V | 0.050 | 1374.3 | 0.8014 | 56 |
| PG 70%, Ethanol$^b$ 20%, qs with Water | 0.446 | 155.5 | 0.9683 | 119 |
| PG 70%, Ethanol$^b$ 20%, qs with Buffer | 0.226 | 306.2 | 0.9808 | 119 |
| Buffer (pH 5.4) | 0.531 | 130.4 | 0.9375 | 26 |

$^a$Correlation coefficient of the linear regression line.
$^b$Ethanol
*See Example I

EXAMPLE VI

Stability of Methyl 3-(p-Phenoxypropanolamine) propionate (the drug) in Vehicles Containing Sodium Acetate Buffer, Ethanol and Propylene Glycol (PG)

Stability of the drug (100 mg/ml) was tested in vehicles containing 0.1M sodium acetate buffer, 0% Ethanol, and 10% Propylene glycol under various storage conditions for different time periods.

Stability results are given in Tables VII and VIII. The data indicates that the rate of degradation is temperature dependent. No change in physical appearance was observed during the experiment.

TABLE VII

Potency of the Drug Over Time in Various Environments

| Environment | Storage, Months | % of Labeled Amount | % Change From Initial |
|---|---|---|---|
| | Initial | 100.7 | — |
| 55° C. | $\frac{1}{2}$ | 101.3 | +0.6 |
| | 1 | 89.3 | −11.4 |
| | 1$\frac{1}{2}$ | 94.3 | −6.4 |
| | 2 | 90.7 | −10.0 |
| 40° C. | 1 | 99.9 | −0.8 |
| | 3 | 99.8 | −0.9 |
| | 6 | 95.8 | −4.9 |
| 15–30° C. | 1 | 102.7 | +2.0 |
| | 3 | 101.5 | +0.8 |
| | 6 | 95.8 | −4.9 |
| LC* | $\frac{1}{2}$ | 102.8 | +2.1 |

*High intensity light cabinet (600–1200 Foot Candles)

TABLE VIII

Physical Appearance and pH of the Drug Over Time in Various Environments

| Environment | Storage, Months | pH | pH Change From Initial | Appearance |
|---|---|---|---|---|
| | Initial | 5.0 | — | Clear, faint yellowish solution |
| 55° C. | $\frac{1}{2}$ | 4.8 | −0.2 | Clear, faint yellowish solution |
| | 1 | 4.8 | −0.2 | Clear, faint yellowish solution |
| | 1$\frac{1}{2}$ | 4.8 | −0.2 | Clear, faint yellowish solution |
| | 2 | 4.7 | −0.3 | Clear, faint yellowish solution |
| 40° C. | 1 | 4.9 | −0.1 | Clear, faint yellowish solution |
| | 3 | 4.9 | −0.1 | Clear, faint yellowish solution |
| | 6 | 4.7 | −0.3 | Clear, faint yellowish solution |
| 15–30° C. | 1 | 5.0 | 0 | Clear, faint yellowish solution |
| | 3 | 4.9 | −0.1 | Clear, faint yellowish solution |
| | 6 | 4.9 | −0.1 | Clear, faint yellowish solution |
| LC* | $\frac{1}{2}$ | 4.9 | −0.1 | Clear, faint yellowish solution |

*High intensity light cabinet (600–1200 Foot Candles)

EXAMPLE VII

Stability on Methyl 3-(p-Phenoxypropanolamine) Propionate (the drug) in Vehicles Containing Sodium Acetate Buffer, Ethanol and Propylene Glycol Stability of the drug (100 mg/ml) was tested in vehicles containing 0.1M sodium acetate buffer, 10% Ethanol and 10% Propylene glycol under various storage conditions for different time periods.

Stability results are given in Tables IX and X. The data indicates that the rate of degradation is temperature dependent. No change in physical appearance was observed during the experiment.

TABLE IX

Potency of the Drug Over Time in Various Environments

| Environment | Storage, Months | % of Labeled Amount | % Change From Initial |
|---|---|---|---|
| | Initial (3-24-82) | 99.2 | — |
| 55° C. | $\frac{1}{2}$ | 96.6 | −2.6 |
| | 1 | 90.0 | −9.2 |
| | 2 | 90.4 | −8.8 |
| 40° C. | 1 | 95.1 | −4.1 |
| | 3 | 94.2 | −5.0 |
| | 6 | 90.4 | −8.8 |
| 15–30° C. | 1 | 99.8 | +0.6 |
| | 3 | 97.3 | −1.9 |
| | 6 | 98.1 | −1.1 |
| 5° C. | 3 | 98.5 | −0.7 |
| | 6 | 98.8 | −0.4 |
| LC* | $\frac{1}{2}$ | 98.7 | −0.5 |
| NL** | 3 | 97.3 | −1.9 |
| | 6 | 97.5 | −1.7 |

*High intensity light cabinet (600–1200 Foot Candles)
**Eastern diffuse sunlight

TABLE X

Physical Appearance and pH of the Drug Over Time in Various Environments

| Environment | Storage, Months | pH | pH Change From Initial | Appearance |
|---|---|---|---|---|
| | Initial (3-24-82) | 5.1 | — | Clear, faint yellowish solution |
| 55° C. | $\frac{1}{2}$ | 5.1 | 0 | Clear, faint yellowish solution |
| | 1 | 5.0 | −0.1 | Clear, faint yellowish solution |
| | 2 | 5.0 | −0.1 | Clear, faint yellowish solution |
| 40° C. | 1 | 5.1 | 0 | Clear, faint yellowish solution |
| | 3 | 4.9 | −0.2 | Clear, faint yellowish solution |
| | 6 | 4.9 | −0.2 | Clear, faint yellowish solution |
| 15–30° C. | 1 | 5.1 | 0 | Clear, faint yellowish solution |
| | 3 | 4.9 | −0.2 | Clear, faint yellowish solution |
| | 6 | 5.1 | 0 | Clear, faint |

TABLE X-continued

Physical Appearance and pH of the Drug Over Time in Various Environments

| Environment | Storage, Months | pH | pH Change From Initial | Appearance |
|---|---|---|---|---|
| 5° C. | 3 | 5.0 | −0.1 | Clear, faint yellowish solution |
| | 6 | 5.1 | 0 | Clear, faint yellowish solution |
| LC* | ½ | 5.3 | +0.2 | Clear, faint yellowish solution |
| NL** | 3 | 5.0 | −0.1 | Clear, faint yellowish solution |
| | 6 | 5.0 | −0.1 | Clear, faint yellowish solution |

*High intensity light cabinet (600–1200 Foot Candles)
**Eastern diffuse sunlight

EXAMPLE VIII

Stability of

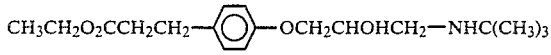

In Hydroalcoholic Solution Over Time

An amount of the above compound sufficient to give a final concentration of 100 mg/ml is dissolved in a vehicle containing acetate buffer, ethanol and propylene glycol such that the molar ratio of the compound to the acetate buffer is 3:1, the volume ratio of the ethanol to the propylene glycol is 1:1, and the pH is 5.0. The solution is filled into 5 ml flint ampuls (3 ml solution per ampul). The ampuls are sealed and placed in a 40° C. oven for 6 months. The compound is stable in this composition.

EXAMPLE IX

Stability of

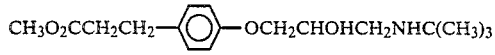

In Hydroalcoholic Solution over Time

An amount of the above compound sufficient to give a final concentration of 100 mg/ml is dissolved in a vehicle containing acetate buffer, ethanol and propylene glycol such that the molar ratio of the substance to the acetate buffer is 3:1, the volume ratio of the ethanol to the propylene glycol is 1:1, and the pH is 5.0. The solution is filled into 5 ml flint glass ampuls (3 ml per ampul). The ampuls are sealed and placed in a 40° C. oven for 6 months. The compound is stable in this composition.

We claim:

1. A pharmaceutical composition for parenteral administration comprising the β-adrenergic compound

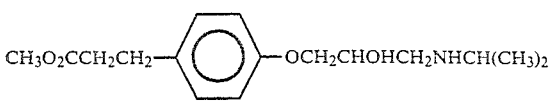

or its pharmaceutically acceptable salts in an aqueous solution comprising from about 5 to about 60% by volume ethanol; from about 5 to about 60% by volume propylene glycol, and from about 0.5 to about 2 molar physiologically acceptable buffering agent, said solution having a pH of from about 4.0 to about 6.0.

2. The composition of claim 1, wherein said solution comprises about 25% propylene glycol by volume, about 25% ethanol by volume and said buffering agent comprises sodium acetate and glacial acetic acid.

3. The composition of claim 2, wherein said pH is from about 4.5 to about 5.5.

4. A method for stabilizing a β-adrenergic blocking compound having the formula

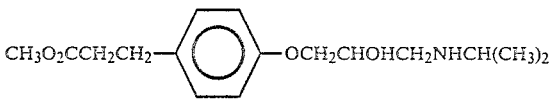

or its pharmaceutically acceptable salts, comprising storing said compound in an aqueous solution comprising from about 0.1 to about 30% by weight of said compound, from about 0.05 to about 2 molar physiologically acceptable buffering agent, from about 5 to about 60% volume ethanol and from about 5 to about 60% by volume propylene glycol, said solution having a pH of from about 4.0 to about 6.0.

5. The method of claim 4, wherein said solution comprises about 25% by volume ethanol and about 25% by volume polypropylene glycol and said buffering agent comprises sodium acetate and glacial acetic acid.

6. The method of claim 5, wherein the pH of said solution is from about 4.5 to about 5.5.

7. A pharmaceutical composition for parenteral administration comprising from about 10 to about 25% by weight of a β-adrenergic compound having the formula

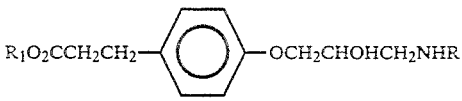

wherein $R_1$ is ethyl or methyl and R is alkyl having from about 1 to about 6 carbon atoms; or its pharmaceutically acceptable salts in an aqueous solution further comprising from about 5 to about 60% by volume ethanol; from about 5 to about 60% by volume propylene glycol; and a physiologically acceptable buffer, said solution having a pH of from about 4.6 to about 5.4.

8. The composition of claim 7, wherein said buffer comprises sodium acetate.

9. The composition of claim 8, wherein said buffer further comprises glacial acetic acid.

10. The composition of claim 9, wherein said solution comprises about 25% by volume ethanol and about 25% by volume propylene glycol.

* * * * *